United States Patent [19]

Gunkel et al.

[11] Patent Number: 4,837,373

[45] Date of Patent: Jun. 6, 1989

[54] TEST STRIPS

[75] Inventors: Werner Gunkel, Rossdorf; Helmuth Krauss, Bensheim, both of Fed. Rep. of Germany

[73] Assignee: Merck Patent Gesellschaft mit Beschränkter Haftung, Darmstadt, Fed. Rep. of Germany

[21] Appl. No.: 48,696

[22] Filed: May 12, 1987

[30] Foreign Application Priority Data

May 13, 1986 [DE] Fed. Rep. of Germany ........ 3616105

[51] Int. Cl.⁴ .................. G01N 21/77; G01N 33/52
[52] U.S. Cl. .......................... 422/56; 422/57; 436/169; 435/805
[58] Field of Search .............. 422/55, 56, 57, 58, 422/61, 66; 436/169, 170; 435/805

[56] References Cited

U.S. PATENT DOCUMENTS

| | | | |
|---|---|---|---|
| 2,918,893 | 12/1959 | Norton | 422/56 X |
| 3,507,269 | 4/1970 | Berry | 422/56 X |
| 3,802,842 | 4/1974 | Lange et al. | 422/57 X |
| 4,042,329 | 8/1977 | Hochstrasser | 422/58 X |
| 4,092,115 | 5/1978 | Rupe et al. | 422/56 X |
| 4,181,500 | 1/1980 | Cowsar | 422/56 X |
| 4,205,043 | 5/1980 | Esch et al. | 422/58 X |
| 4,518,565 | 5/1985 | Boger et al. | 436/169 X |
| 4,582,684 | 4/1986 | Vogel et al. | 422/57 |
| 4,604,264 | 8/1986 | Rothe et al. | 435/805 X |
| 4,618,475 | 10/1986 | Wang | 435/805 X |

Primary Examiner—Robert J. Hill, Jr.
Attorney, Agent, or Firm—Millen & White

[57] ABSTRACT

The invention relates to test strips for the detection of substances present in liquids and comprises a firm support and matrices impregnated with reagents. The matrices are spaced from one another on the support by means of adhesive strips, and the adhesive strips are covered with strips of film.

9 Claims, 1 Drawing Sheet

TEST STRIPS

BACKGROUND OF THE INVENTION

The invention relates to test strips for the detection of substances present in liquids. More particularly, the invention relates to a firm support and at least one absorbent matrix impregnated with reagents, with the at least one matrix being attached to the support in areas outside the zone used for evaluation.

Test strips have been used for a long time for qualitative detection of various substances in solution and also, to an increasing extent, in combination with evaluation devices, for the quantitative detection of such substances. Test strips of this type consist, as a rule, of a small plastic bar with matrices or reaction zones fastened to the lower region thereof in the form of papers impregnated with reagents, films coated with reagents or special layers containing the reagent. Various methods are used for fastening the reaction zones to the support. A common method is, for example, to fasten the reaction zone by means of adhesives applied underneath the zone. The selection of adequately inert adhesives causes problems in this regard - particularly in the case of the reagents and enzymes, such as those used in clinical chemistry, which are often very sensitive. A further customary method is mechanical clamping of the reaction zones by means of plastic nets stretched over the zones (German Patent Specification 2,118,455). The impaired view of the surface of the reaction zone caused by the net is a disadvantage in this regard. During evaluation of a device, the network has a disturbing effect on the evaluation. In addition, it is difficult to prevent reaction zones, from falling out sideways during use.

SUMMARY OF THE INVENTION

An object of the present invention is to provide test strips in which evaluation zones are free from the effects of the elements used for fastening, such zones to the support, such as adhesives or nets stretched over the zones.

Accordingly, the invention relates to test strips for the detection of substances present in liquids, wherein the test strips include a firm support and matrices impregnated with reagents, wherein the matrices are spaced from one another on the support by means of adhesive strips, with the adhesive strips being covered with strips of film.

In a further embodiment of the invention, the surface of the matrices facing away from the support is covered with a film which is perforated in the region of the evaluation zone. The films can be either transparent or opaque; preferably they are opaque. Preferably the films should expose at least 50% of the evaluation zone of the matrices.

BRIEF DESCRIPTION OF THE DRAWINGS

Various other objects, features and attendant advantages of the present invention will be appreciated as the same becomes better understood when considered in connection with the accompanying drawings, in which like reference characters designate the same or similar parts throughout the several views, and wherein.

DETAILED DESCRIPTION

Figure 1:
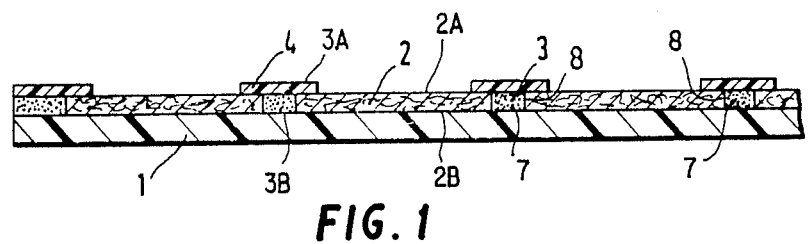
FIG. 1 is a side elevation of a test strip according to the instant invention taken along line 1—1 of FIG. 2.
Figure 2:
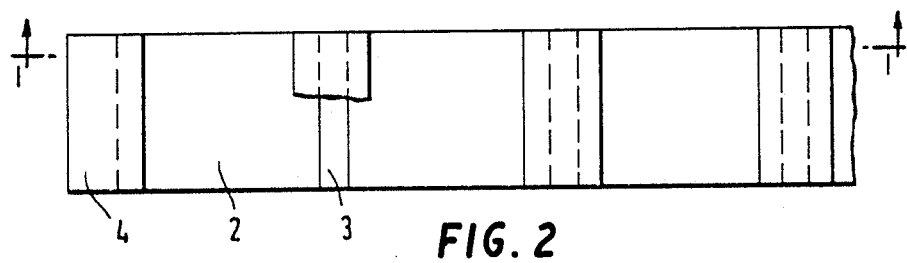
FIG. 2 is a top view of the test strip of FIG. 1.
Figure 3:
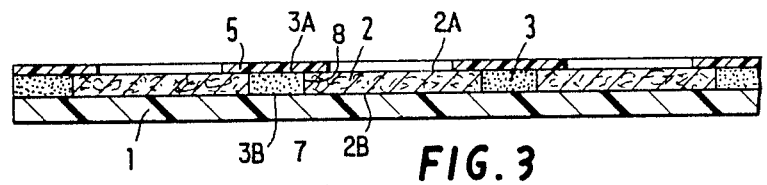
FIG. 3 is a side elevation of a second embodiment of a test strip configured in accordance with the principles of the instant invention taken alone line 3—3 of FIG. 4.
Figure 4:
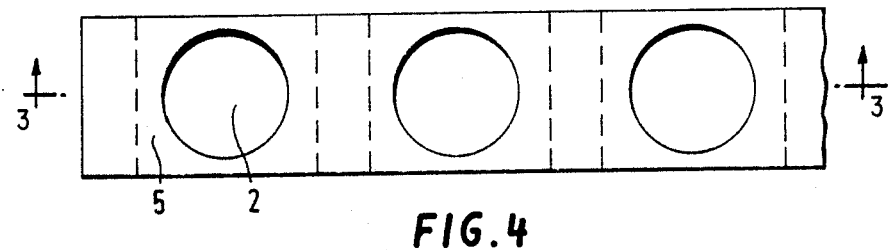
FIG. 4 is a top view of the test strip of FIG. 3.

FIGS. 1-4 show the assembly of two embodiments of the test strips according to the invention. Each of the FIGS. 1 and 3 show an enlarged cross-section of the lower part of a test strip according to the invention. FIGS. 2 and 4 show a corresponding plan view in an enlarged presentation. The firm support or substrate is marked 1, the matrices or reaction zones are marked 2, the adhesive strips between the matrices are marked 3, the film strips present as a covering over the adhesive strips 3 are marked 4, and the perforated film is marked 5.

Substrate 1 extends in lateral and longitudinal directions and the strips of adhesive material 3 extend laterally and are spaced longitudinally with respect to one another.

FIGS. 1 and 2 show a test strip in which the matrices 2 are fixed in their position on the support or substrate 1 by means of adhesive strips 3 applied between the matrices and adhered to the support. The adhesive strips 3 bond to the matrices 2 adjacent the edges thereof. To ensure reliable attachment to the support 1 and to cover the zones of the matrices affected by the adhesive, these zones are provided with film strips 4 which, in addition, also overlap the marginal regions of the matrices.

FIGS. 3 and 4 show an embodiment in which the whole surface is covered with a film 5 which film is perforated in each case in the region of the reaction zones. The film is glued to the adhesive strips 3 between the reaction zones and is glued to the support 1 in the region of handling. The reagent zones used for evaluation thus have no contact at all with the adhesive and have a completely free surface.

Possible solid supports 1 are the customary strips of film composed of plastics, such as, for example, polystyrene, polyvinyl chloride, polyesters or polyamides. However, supports composed of metal films, for example aluminum, or supports composed of glass are also very suitable.

The absorbent matrices 2 which are impregnated with reagents are made of, for example, filter paper, nonwovens, fabrics made from natural or synthetic fibers, porous gels or laminations of these materials. Films coated with reagents or reagents incorporated in plastic are also very suitable for special purposes.

The adhesive strips 3 at the upper and lower end of the matrix or between the individual matrices consist of the customary hot-melt adhesives or cold-bonding adhesives. It is preferable to use hot-melt adhesives to prepare the test strips according to the invention in a simple and economical manner. The adhesive strips are about 0.5-3 mm, preferably 1-2 mm, wide and their principal purpose is to fix the matrices in their position on the solid support.

In accordance with the invention, both the adhesive strips and the upper and lower marginal zones of the matrices which come into contact with the adhesive are covered by strips of film 4. These film strips preferably consist of a non-transparent, hydrophobic material, such as polyester or polystyrene, or of paper 50-100 μm thick which has been rendered hydrophobic. They should cover the marginal zones of the matrices to the extent of about 0.5–1 mm and thus bind it to the firm support.

The perforated film 5 used in the embodiment shown in FIGS. 3 and 4 consists of the same material as the film strips which have been described. The shape of the perforation is not critical; it can be circular, square, rectangular or polygonal. In the case of a circular perforation, the diameter of the perforation should be about 1 mm smaller than the width or length of the area of matrix below it; in any event, the film should leave at least 50%, preferably up to 90% of the matrix area, the so-called evaluation zone, free.

The dimensions of the test strips according to the invention shown in FIGS. 1 and 2 correspond to those of commercially available test strips. The width of the matrix is about 7.5 mm, the distance between the individual matrices, i.e., the width of the adhesive strip is about 1.5 mm and the width of the film strips is about 3 mm. In this case about 20%, for example, of a square matrix is covered by the strips of film.

The test strips according to the invention are prepared on customary hot-melt adhesive sealing equipment. The liquified hot-melt adhesive 3 which is preferably based on polyethylene and/or polyvinylacetate, is applied in the form of lines to the support 1. The strips of matrix 2 impregnated with reagents are inserted between the adhesive strips 3 which have not yet hardened completely. The film strips 4 or the perforated film 5 are fed in immediately behind these. The individual components are pressed onto the support by means of a back-up roller. A firm bond between the support 1, the matrix 2 and the covering film 4 or perforated film 5 is formed in this way in the region of the adhesive. The band prepared by this method is then cut in a customary manner into strip approximately 6–8 mm wide by means of a guillotine-type cutting device.

In summary, both the embodiment of FIGS. 1 and 2 and that of FIGS. 3 and 4 include the concept of a single layer absorbent matrix pad 2 having a front surface 2A and a back surface 2B wherein the back surface 2B abuts the substrate 1. The adhesive strips 3 each also have a front surface 3A which is substantially coplanar with the front surface 2A of the absorbent matrix pads 2 and a rear surface 3B which is adhered to the substrate 1. The absorbent matrix pads 2 and adjacent adhesive strips 3 each have edge portions 7 and 8 respectively which abut one another so that the only area of adhesion is where the edge portions abut one another. In that the abutting edge portions 7 and 8 are overlapped by the film strips 4 or the perforated film 5 which is adhered to the front surfaces 3A of the adhesive strips, any effect of the adhesive on the interaction between the selected substances and the liquid into which the test strip is dipped and the reagents within the absorbent matrix pads is minimized.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A test strip for detecting a substance present in a liquid, wherein the test strip comprises:

a substrate having a top surface;

at least one single layer absorbent matrix pad which is impregnated with reagents for reacting with a selected substance in a liquid, each single layer absorbent matrix pad having an exposed front surface which defines an evaluation zone for facing a liquid and for displaying results of a reaction between a selected substance and the reagents impregnated therein, a back surface which directly abuts with the top surface of the substrate, and edges extending between its front and back surfaces;

at least two adhesive strips adjacent each single layer absorbent matrix pad, each adhesive strip having a back surface which directly abuts with the top surface of the substrate, a front surface which is complanar with the front surface of single layer absorbent matrix pads adjacent thereto, and side edges, with at least one side edge of each adhesive strip being adhered substantially to a side edge of absorbent matrix pads adjacent thereto, and wherein each single layer absorbent matrix pad only contacts adhesive along its edges;

a layer of film material corresponding to each adhesive strip, with each layer of film material adhered to and completely covering its corresponding adhesive strip and having an edge portion overlapping edges of single layer absorbent matrix pads which are adhered substantially to an edge of its corresponding adhesive strip in such a manner that a substantial portion of the evaluation zone of each single layer absorbent matrix pad is visually unobstructed.

2. The test strip of claim 1, wherein the substrate extends in a lateral and a longitudinal direction, each adhesive strip has a width with respect to the longitudinal direction of the substrate in the range of 0.5 to 3 mm, each single layer absorbent matrix pad has a width with respect to the longitudinal direction of the substrate of about 7.5 mm, and each layer of film material has a width with respect to the longitudinal direction of the substrate of about 3 mm.

3. The test strip of claim 1, wherein at least 50% of the evaluation zone of each single layer absorbent matrix pad is visually unobstructed.

4. The test strip of claim 3, wherein each layer of film material is opaque.

5. The test strip of claim 1, wherein the edges of each single layer absorbent material are straight.

6. The test strip of claim 5, wherein the strip includes plural single layer absorbent matrix pads.

7. A test strip for detecting a substance present in a liquid, wherein the test strip comprises:

a substrate having a top surface;

at least one single layer absorbent matrix pad which is impregnated with reagents for reacting with a selected substance in a liquid, each single layer absorbent matrix pad having an exposed front surface which defines an evaluation zone for facing a liquid and for displaying results of a reaction between a selected substance and the reagents impregnated therein, a back surface which directly abuts with the top surface of the substrate, and edges extending between its front and back surfaces;

at least two adhesive strips adjacent each single layer absorbent matrix pad, each adhesive strip having a back surface which directly abuts with the top surface of the substrate, a front surface which is coplanar with the front surface of single layer absorbent matrix pads adjacent thereto, and side edges, with at least one side edge of each adhesive strip being adhered substantially to a side edge of absorbent matrix pads adjacent thereto, and wherein each single layer absorbent matrix pad only contacts adhesive along its edges;

a layer of film material adhered to all adhesive strips and completely overlying all adhesive strips and all single layer absorbent matrices, said layer of film material having a continuous opening corresponding to each single layer absorbent matrix pad such that a substantial portion of the evaluation zone of each single layer absorbent matrix pad is visually unobstructed.

8. The test strip of claim 7, wherein each continuous opening is circular.

9. The test strip of claim 8, wherein the strip includes plural single layer absorbent matrix pads.

* * * * *